US00PP08098P

United States Patent [19]

Mojonnier

[11] Patent Number: Plant 8,098

[45] Date of Patent: Jan. 12, 1993

[54] ALSTROEMERIA PLANT NAMED LETICIA

[76] Inventor: Erwin Mojonnier, 237 Quail Dr., Encinitas, Calif. 92024

[21] Appl. No.: 720,674

[22] Filed: Jun. 25, 1991

[51] Int. Cl.[5] ..... A01H 5/00
[52] U.S. Cl. ..... Plt./87.1
[58] Field of Search ..... Plt./87.1

*Primary Examiner*—James R. Feyrer
*Attorney, Agent, or Firm*—Foley & Lardner

[57] ABSTRACT

A new and distinct cultivar of Alstroemeria plant named Leticia, characterized by its low maintenance, November flowering through photoperiodic control, good post-harvest color retention, ease of propagation, and by its flowers which have a bright red-purple background with heavy dark red streaking on the upper petals and a few streaks on the lower petals, and patches of yellow on the upper petals.

1 Drawing Sheet

The present invention relates to a new and distinct cultivar of Alstroemeria plant hereinafter referred to by the cultivar name Leticia.

Leticia is a product of a planned breeding program which had the primary objectives of creating new Alstroemeria cultivars having unique flower color and being capable of early winter production with low maintenance requirements. The latter term refers to the production of a minimum of non-flowering stems.

In order to fully understand an important characteristic of the new cultivar, an explanation of typical current winter production schedules for cut flowers of Alstroemerias would be helpful. Standard industry growing practices normally utilize only natural daylight. As a result, late fall and winter production of Alstroemeria cut flowers, due to reduced levels of light during these periods, typically requires 12 weeks or more of growing time from the planting of the rhizome cutting to the initiation of flowering. Even more time is required for further flowering to produce a stem ready for sale. With certain varieties, the period of time from planting to flowering can extend up to almost six months. This time will substantially vary from variety to variety, and growing techniques and conditions also affect the growing period. For example, a larger cutting will obviously require a shorter growing time than a relatively small cutting. High temperatures normally have an adverse affect on growth, as does reduced light.

The commercial implications of relatively slow growth characteristics under natural light conditions should be obvious. Increased bench or field time (if grown outdoors where climates permit) substantially increases production costs, which in turn result in increased costs per stem due to the increased cost of production. Total production of Alstroemeria cut flowers during such period is also correspondingly less. This adversely affects the normal supply/demand ratio in the marketplace, and as a result cut flowers of Alstroemeria are substantially more costly during the winter months than during the periods beginning in March when production increases. It is not unusual for stem prices to be 50% higher during the winter months of December, January, and February.

The inventor has discovered that through photoperiodic growth practices, certain cultivars can be brought into flowering in the late fall and winter periods in substantially reduced periods of time, thereby increasing production during these periods. However, all cultivars are not adaptable to photoperiodic control.

Through extensive breeding, the inventor has been able to produce new Alstroemeria cultivars, of which Leticia is one, specifically adaptable to photoperiodic control. The inventor's preferred growing technique includes growing the newly stuck plants under natural light conditions for approximately one month without light supplement. After approximately one month, the day length is effectively increased by providing four hours of artificial lighting by techniques or methods well known in the industry.

A preferred growing regimen which has provided excellent results comprises planting established rhizome divisions in ground beds near the end of August or first of September. Beginning approximately one month after planting, and continuing to April 1, the plants are subjected to light from 2:00 a.m. to 6:00 a.m. daily. A lighting system which has proved highly effective consists of 135 watt bulbs spaced every 10 feet, and hung approximately 7 feet above the ground. The rhizome divisions are positioned in rows that are spaced 12 feet apart.

By effectively increasing the day length by means of artificial lighting, flowering can be initiated in a much shorter time. Within approximately six (6) weeks the first flower appears, and saleable stems are ready from mid-November to mid-December, depending upon the variety. In many instances, flowering is essentially continuous until June when the stems are too short to sell as cuts without heavy shading and some method of cooling. Without shading and cooling to prolong commercial stem production, it is common practice to dig up and divide the plants. The divided plants are then stuck in late August or early September as described, and the cycle repeated. It has also been noted that the increased light regimen has resulted in longer stems, a very desirable quality.

Leticia was originated by the inventor Erwin Mojonnier from a hybridization made in a controlled breeding program in Encintas, Calif. in 1988. The female parent was a cultivar identified as L5, a short plant with a hot pink color, streaking on the upper and lower petals, and having a yellow patch on the upper petals. The male parent was a cultivar identified as L11, a tall plant with a hot pink flower color, sparse streaking on the upper and lower petals, and with a faint yellow patch against a white throat on the upper petals.

Leticia was discovered and selected as one flowering plant within the progeny of the stated parentage by the inventor in May, 1988, in a controlled environment in Encinitas, Calif.

The first act of asexual reproduction of Leticia was accomplished when vegetative cuttings were taken by the inventor from the initial selection in August, 1988, in a controlled environment in Encinitas, Calif. Horticultural examination of selected units initiated in 1989 has demonstrated that the combination of characteristics as herein disclosed for Leticia are firmly fixed and retained through successive generations of asexual reproduction.

Leticia has not been observed under all possible environmental conditions. The phenotype may vary significantly with variations in environment such as temperature, light intensity and day length. The following observations, measurements and comparisons describe plants grown in Encinitas, Calif. under greenhouse conditions which approximate those generally used in commercial practice.

The following traits have been repeatedly observed and are determined to be basic characteristics of Leticia, which in combination distinguish this Alstroemeria as a new and distinct cultivar:

1. Low maintenance, with a low number of non-flowering stems produced per plant.
2. Very early winter production beginning in November based on the photoperiodic control program described above.
3. Leticia is easily propagated.
4. Leticia possesses a good post-harvest color retention.
5. Leticia has a unique combination of petal color, streaking and patching.

The accompanying color photographic drawing shows typical inflorescence and foliage characteristics of Leticia, with colors being as nearly true as possible with illustrations of this type. The photograph is a top perspective close-up view of a few flowers and surrounding foliage. Clearly visible are Leticia's large pink flowers with streaks on the upper two petals and a few random streaks on the lower petal, and a patch of yellow on the upper two petals.

In the following description, color references are made to The Royal Horticultural Society Color Chart (RHS). The color values were determined between 8:30 and 9:15 a.m. on Apr. 26, 1990 under 80 foot candles of light intensity at Encinitas, Calif.

Classification:

*Botanical.*—Alstroemeria cv Leticia.

*Commercial.*—Alstroemeria.

PLANT

Form: Cut flower.
Height: Approximately 102 cm. at time of harvest.
Propagation: Originates from rhizome.
Foliage:
*Quantity.*—21 leaves per stem.
*Size of leaf.*—14.1 cm. long and 2.3 cm. wide.
*Shape of leaf.*—Lanceolate.
*Color.*—Upper side, green 137A; under side, green 137C.
Rhizomes:
*Color.*—White, 155B.
*Size.*—1 cm. by 1 cm.

INFLORESCENCE

Bud:
*Form.*—Indeterminate.
*Diameter.*—1.6 cm.
*Length.*—4.2 cm.
*Calyx.*—4.6 mm.
*Peduncle.*—10.2 cm. in length.
*Color.*—Green, 138B.
Flower:
*Size.*—6.5–7 cm. in diameter.
*Borne.*—5 flowers per umbel.
*Blooming habit.*—Very early; begins flowering in November when a photoperiodically controlled regimen is followed.
*Shape.*—Asymmetrical.
Color:
*Upper surface.*—Red-purple 57C.
*Under surface.*—Red-purple 57D.
*Other notations.*—The upper two petals are heavily streaked with grey-purple 187A, with the lower petal having a few streaks of the same color. The upper two petals also have patches of yellow 2B, and contain white 155D in the lower third.
Peduncle: Length, 11.7 cm.; color, green 137C.
Lasting quality: Cut flowers last 14 days.

REPRODUCTIVE ORGANS

Stamens: Number, 6.
Anthers: Color, gray-brown 199B.
Filaments: Color, red-purple 62B.
Pistils: Number, 1; color red-purple 62B.
Stigma: Color, red-purple 62B.

I claim:

1. A new and distinct cultivar of Alstroemeria plane named Leticia, as illustrated and described.

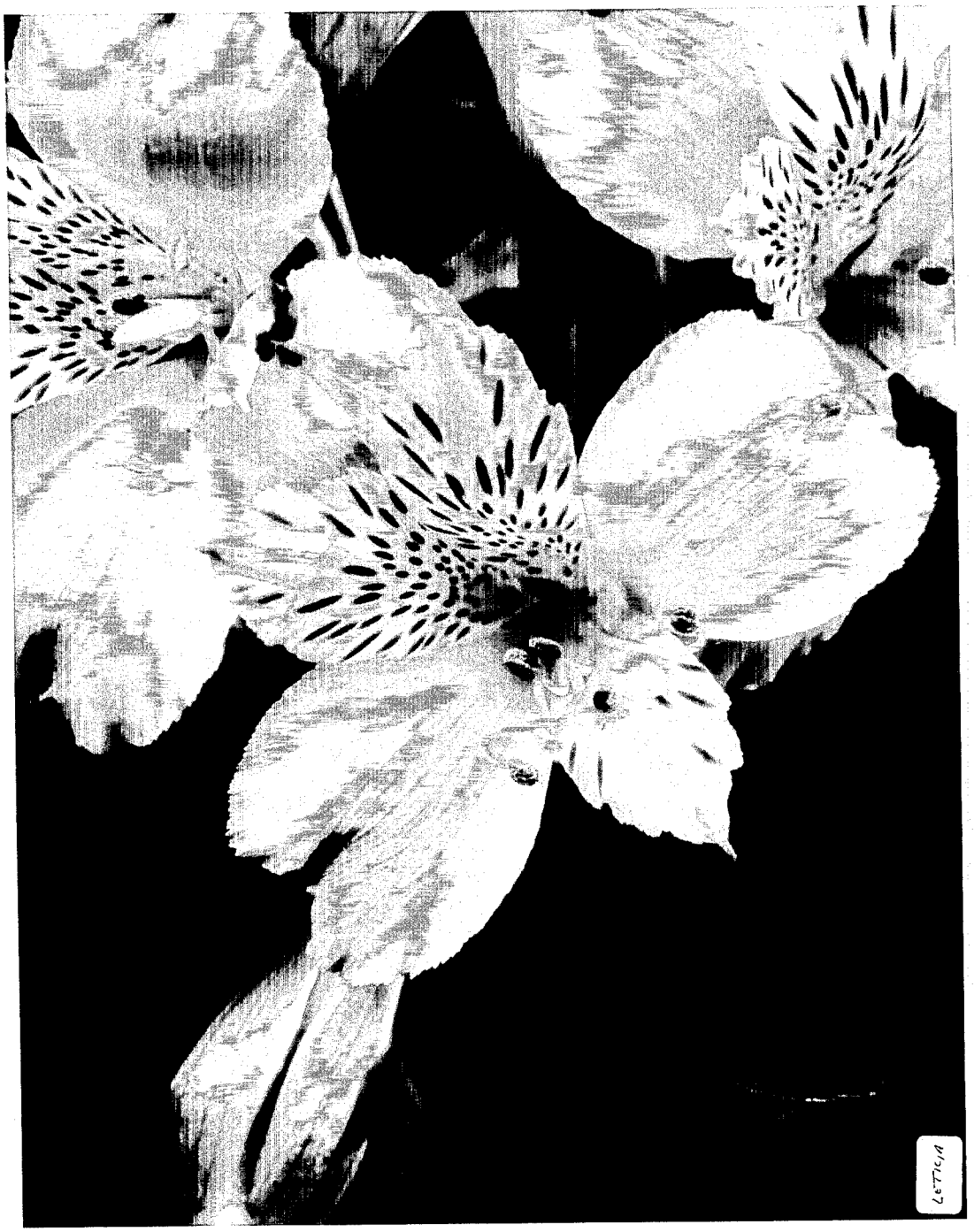

* * * * *